US012599780B2

(12) United States Patent
Seifert et al.

(10) Patent No.: US 12,599,780 B2
(45) Date of Patent: Apr. 14, 2026

(54) LASER THERAPY DEVICE FOR THERAPY OF A LIVING TISSUE

(71) Applicant: MEDIZINISCHES LASERZENTRUM LÜBECK GMBH, Lübeck (DE)

(72) Inventors: Eric Seifert, Lübeck (DE); Ralf Brinkmann, Lübeck (DE); Hossameldin Abbas, Lübeck (DE)

(73) Assignee: MEDIZINISCHES LASERZENTRUM LÜBECK GMBH, Lübeck (DE)

( * ) Notice: Subject to any disclaimer, the term of this patent is extended or adjusted under 35 U.S.C. 154(b) by 207 days.

(21) Appl. No.: 18/262,526

(22) PCT Filed: Feb. 4, 2022

(86) PCT No.: PCT/EP2022/052669
§ 371 (c)(1),
(2) Date: Jul. 21, 2023

(87) PCT Pub. No.: WO2022/167562
PCT Pub. Date: Aug. 11, 2022

(65) Prior Publication Data
US 2024/0100355 A1 Mar. 28, 2024

(30) Foreign Application Priority Data
Feb. 5, 2021 (DE) .................... 10 2021 201 080.6

(51) Int. Cl.
*A61N 5/067* (2006.01)
*A61B 17/00* (2006.01)
(Continued)

(52) U.S. Cl.
CPC ........... *A61N 5/067* (2021.08); *A61N 5/0625* (2013.01); *A61B 2017/0019* (2013.01);
(Continued)

(58) Field of Classification Search
CPC .................. A61N 5/067; A61N 5/0625; A61B 2017/0019; A61B 2018/00702;
(Continued)

(56) References Cited

U.S. PATENT DOCUMENTS

2006/0111697 A1     5/2006  Brinkmann et al.
2013/0102894 A1*    4/2013  Birngruber .......... A61B 5/0066
                                                       600/425

OTHER PUBLICATIONS

Muller et al. "Imaging thermal expansion and retinal tissue changes during photocoagulation by high speed OCT," Biomedical Optics Express, May 2012, vol. 3, No. 5, 22 pages.
(Continued)

*Primary Examiner* — Ankit D Tejani
*Assistant Examiner* — Sebastian X Lukjan
(74) *Attorney, Agent, or Firm* — Sheridan Ross P.C.

(57) ABSTRACT

A laser therapy device comprises a pulsed laser light source. Each triggering of tissue irradiation causes application of a first heating laser pulse of a first power and a first pulse duration and at least a second heating laser pulse of a second power and a second pulse duration to the tissue. Changes in volume resulting from the rising and the decreasing power gradient of the first laser pulse are detected. The therapy device, on the basis of the measured values relative to the change in volume and taking into consideration at least the predetermined rises of the power gradients of the first heating laser pulse, determines an estimated value for the temperature increase in the tissue during irradiation of the first heating laser pulse, and generates, from the estimated value, a command that causes adjustment of the second power and/or the second pulse duration of the second laser pulse.

10 Claims, 5 Drawing Sheets

(51) Int. Cl.
    *A61B 18/00*        (2006.01)
    *A61N 5/06*         (2006.01)
    *A61F 9/008*        (2006.01)

(52) U.S. Cl.
    CPC ............... *A61B 2018/00702* (2013.01); *A61B*
            *2018/00761* (2013.01); *A61B 2018/00803*
            (2013.01); *A61F 2009/00863* (2013.01)

(58) Field of Classification Search
    CPC . A61B 2018/00761; A61B 2018/00803; A61F
            2009/00863; A61F 9/00821; A61F 9/008;
                           A61F 2009/00844
    See application file for complete search history.

(56) References Cited

OTHER PUBLICATIONS

International Search Report and Written Opinion for International
(PCT) Application No. PCT/EP2022/052669, dated May 30, 2022,
10 pages.
English Translation of the International Search Report for International (PCT) Patent Application No. PCT/EP2022/052669, dated
May 30, 2022, 2 pages.

* cited by examiner

LASER THERAPY DEVICE FOR THERAPY OF A LIVING TISSUE

CROSS REFERENCE TO RELATED APPLICATIONS

This application is a national stage application under 35 U.S.C. 371 and claims the benefit of PCT Application No. PCT/EP2022/052669 having an international filing date of 4 Feb. 2022, which designated the United States, which PCT application claimed the benefit of German Patent Application No. 10 2021 201 080.6 filed 5 Feb. 2021, the disclosures of each of which are incorporated herein by reference in their entireties.

The invention relates to a device for the laser therapy of a living tissue, comprising a pulsed laser light source and automatic regulation of the power irradiated in. The invention also relates in particular to an ophthalmological laser device for the therapy of the back of the eye.

Lasers are used for the treatment of various retinal disorders. During the laser irradiation of the back of the eye, primarily the light-absorbing layers, the retinal pigment epithelium (RPE) and choroid are heated, from where the heat spreads into the adjoining layers. In addition to the absorbed laser energy, this spreading depends on the pulse duration and the irradiated area. Per laser spot on the retina, the typical area is around 100-500 µm in diameter with an irradiation duration of usually 20-500 ms. The shorter the irradiation time, the less heat diffuses into the volume outside the irradiated region.

Depending on the therapeutic aim, different temperatures are desirable in order avoid under-treatment, i.e. the lack of therapeutic effect, or over-treatment, i.e. unintentional collateral damage. In the stated time range, for the sub-lethal stimulation of the retina approximately 43-50° C. are required (e.g. hyperthermic tissue stimulation for the prophylactic therapy of dry age-related macular degeneration, AMD), for sub-visible (sub-threshold) 50-70° C. or mild photo-coagulation 70-90° C. (e.g. diabetic maculopathy), for strong photo-coagulation (panretinal irradiation for diabetic retinopathy or retinal detachments) 90-120° C. For the selective thermo-mechanical disruption of RPE (e.g. for retinopathia centralis serosa), nano to microsecond pulses are uses whereby temperatures of >140° C. only occur in RPE (selective retina therapy, SRT) and there results in the selective production of microbubbles on the intracellular melanosomes. As of 2 µs pulse duration, in addition to disruption, thermal necrosis was also observed. In general, pulse durations of between 2 and 50 µs are considered as the transition area between thermomechanical and thermal effects.

Due to the great fluctuations in light transmission through the eye and the very variable light absorption of the RPE (20-80% in the visible spectral range), the aforementioned temperature increases cannot be achieved with fixed laser settings. Therefore, measurement and regulation of the temperature increase during irradiation is absolutely desirable.

For measuring the temperatures, for example from document US 2003/032949 A1, a optoacoustic method is known, in which by means of repetitive short pulsed laser radiation (pulse duration in the nanosecond range, repetition rate typically 1 kHz), which is superimposed on the therapeutic laser radiation, the retinal absorbers are thermoelastically stimulated, and the emitted pressure transients on the cornea of the eye can be picked up by an ultrasonic transducer. Because of the temperature dependency of the Grüneisen coefficient, the pressure amplitudes increase with the retina temperature and, after prior calibration, indicate the current mean temperature increase on the retina. Strictly speaking, temperature determination in this way is only possible as long as the target tissue is only reversibly heated, but not yet thermally converted and permanently damaged. Nonetheless, concepts have been developed to evaluate tissue damage due to a laser pulse sequence ("burst"), and in doing so to determine the temperature during a first partial sequence of the burst in order to regulate the laser during the application of a second partial sequence of the same bust, cf. for example, document US 2010/292763 A1.

The objective is that the treating doctor only has to trigger the laser precisely once for each laser spot to be treated and in doing so can assume that intentional tissue damage occurs just there without causing excessive collateral damage. As a rule, through this "sparing" laser therapy, only weakly or not even visible lesions occur on the retina. In this respect, there is no direct and objective way of checking the effect available to the doctor.

An evident drawback of the method of US 2003/032949 A1 is the necessity of using a separate laser in addition to the therapy laser, which increases the complexity and costs of the laser system.

At present, continuously emitting high-power lasers with emission powers of the order of 10 W in the green spectral band for use on the retina are being developed. In the current context, emission powers of the order of 5 W are covered by the invention. It is expected that in the future, lasers with emission powers of the order of 100 W and approximately constant power over a longer duration will also be available for medical purposes. When using such high powers, the total irradiation time per laser spot must in the lower µs time interval (2-50 µs) or even lower and regulated very well so as not to produce severe, uncontrollable damage on the retina. More particularly, when using such lasers, instead of a laser pulse sequence, a single pulse can already be therapeutically effective.

The very rapid heating of the tissue make it impossible to use an optoacoustic method of the type in US 2003/032949 A1 for temperature control, as the pressure transients always need up to around 20 µs time to go from the retina to an acoustic sensor in a contact glass. The measuring signal would arrive too late to still be able to regulate the heat laser pulse.

Alternatively, optical detection of the transient volume change of the irradiated tissue through reversible thermal expansion and contraction during heating with laser light could be used. Such methods have been tested, for example in the documents US 2013/102894 A1 and US 2015/011983 A1, and use interferometers and, especially envisaged for interferometry, measuring light sources usually reflected into the therapy laser beam. However, here too the drawbacks are primarily in the complexity and costs of the laser system.

Disclosed in the work of Xiaohau Feng et al. "Self-temperature regulation of photothermal therapy by laser-shared photoacoustic feedback", vol. 40, no. 19, 1 October 2015, Optics Letters, pp. 4492-2295, is a laser device with photoacoustic (=optoacoustic) feedback for temperature control of the target with just one heat laser. This laser is operated in a pulse-modulated manner wherein the long heat pulses and the linearly chirped sequence of short pulses for temperature measurement via pressure transients with an ultrasonic transducer continually alternate in time. This results in automatic regulation of the irradiation dose on the target through modulation of the pulse duration of the heat laser so that the target attains and maintains predetermined temperatures with a high degree of precision. In this work, the target is a phantom, the emission power of the laser is 1 W and the laser heat pulses have pulse durations in the millisecond to second range. The chirp sequences takes up 40 microseconds and no time delay to the ultrasonic transducer occurs. These simplified conditions do not allow direct applicability to the problem of retina therapy.

The idea of using the heating laser light itself for temperature determination too, is followed here, as it already was in US 2010/292963 A1. Document DE 10 2009 016184 A1 describes an approach with alternatingly applied short measuring laser pulses and very much longer lasting heating laser pulses from a joint laser source specifically for the laser therapy of the back of the eye under temperature monitoring and regulation.

The work on photoacoustic imaging by Fei Gao et al. "Single laser pulse generates duel photo-acoustic signals for differential contrast photoacoustic imaging", Scientific Reports|7:626|DOI:10.138/s41598-017-00725-4, which appeared online on Apr. 4, 2017 discloses the possibility of photoacoustic imaging of a biological tissue by way of only two pressure transients that are triggered and detected at the start and end of a long heating laser pulse. By dispensing with stress confinement, but maintaining thermal confinement, it is shown that the pressure transients of the start and end of the heating laser pulse have opposite polarities and different amplitudes, which can provide information about the energy density deposited in the tissue during the pulse duration.

Against this background, the first task of the invention is to propose a laser therapy device for the treatment of a living tissue that allows self-regulated, sparing therapy exclusively with laser pulse, i.e. with laser pulses of relatively high power and pulse duration. As a second task of the invention, the device should be further designed to allow objective effect assessment.

The first task is solved by a laser therapy device for the treatment of a living tissue, comprising a pulsed laser light source which emits laser light at an emission power in range of 5 W to 100 W, a device for guiding the laser light into an application, a trigger device for triggering the irradiation of the tissue by means of the applicator, a detection device for measuring time-dependent changes in volume resulting from laser absorption in the tissue, an arithmetic unit for evaluating the detected changes in volume and for outputting control commands to the control device for controlling the power of the laser light irradiated into the tissue, characterised in that a. each triggering of tissue irradiation causes the control unit to apply a first heating laser pulse with a first power and a first pulse duration and at least a second heating laser pulse with second power and a second pulse duration to the tissue at a predetermined pulse interval, wherein b. the detection device, optically or acoustically records the changes in volume resulting from the rising and falling power gradient of the first heating laser pulse and supplies the measured values to the arithmetic unit;

c. the arithmetic unit, on the basis of the measured values of the change in volume and taking into consideration at least the predetermined increase rises of the power gradient of the first heating lase pulse, determines an estimated value for the temperature increase during irradiation of the first heat laser pulse and d. from the estimated value, the arithmetic unit generates a command to the control device that causes the control device to adjust the second power and/or the second pulse duration of the second heating laser pulse so that the irradiation of the second laser pulse heats the tissue to a predetermined target temperature.

The sub-claims relate to advantageous embodiments, more particularly to further developments to assess the effect.

Hitherto, for temperature determination, usually short, low-energy laser pulses have been used which in themselves should not, or only to a small extent, contribute to heating of the tissue. It was generally intended to avoid changing the condition of the tissue during determination of the condition if possible.

The device according to the invention now dispenses with applying short laser pulses or bursts of such laser pulses, and instead only applies long heating laser pulses of medium to high laser power, each of which brings about a temperature increase of several degrees Celsius over its pulse duration. For the treatment of a single laser spot—particularly on the retina—it then only needs very few pulses, preferably even just two.

The first heating laser pulse, which heats a laser spot, should preferably not trigger any lasting tissue damage (e.g. denaturation), but only bring about sufficiently quick volume changes through thermal expansion of the tissue at the start, and contraction at the end of the heating laser pulse, which can be recorded with an optical or acoustic detection device. In doing so, the detection devices produce electrical volume change signals which are sent to an arithmetic unit which can evaluate them.

The detection device can, for example, for the optical recording of movements thermally triggered in the irradiated tissue, be made of light-diffusing or light-reflecting tissue layers and can comprise an interferometer as well as at least one photodetector, which measures a light intensity that changes in time and emits this as measuring values. For this, for example, optical coherence tomography (OCT) can be used or also a high-coherence light source (single longitudinal mode) with speckle recording. The therapy laser itself can also emit light with sufficiently high coherence so that a small proportion of the therapy light can be measuring light at the same time. From the determined movements—such as a change in distance between two diffusing tissue layers—the sought change in volume can be directly inferred.

In accordance with the invention it is preferred that the detection device is configured to record pressure waves triggered thermally in the irradiated tissue and comprises at least one ultrasonic transducer which records a pressure transient and emits it as a measuring value. The ultrasonic waves have sufficient time both during the long pulse and also between the pulses, to propagate from the heated tissue to the ultrasonic receivers.

According to the invention, it is envisaged that the second heating laser pulse, which is only applied after recording and evaluation of the volume change signals, is regulated with the information from the first heating laser pulse.

Preferably the first and second pulse durations are at an interval of 2 to 50 microseconds. Other pulse durations, more particularly shorter ones, are not ruled out. The differentiability—separability—of the volume change signals at the start and end of the pulse is dependent on the type of detection: optical detection also enables this this for very short pulses. In terms of apparatus, acoustic detection is usually simpler.

The pulse interval is usually defined as the time interval between two identical features of two consecutive laser pulses, for example the respective rising pulse gradients or the pulse maxima. On the other hand, in the case of few pulses each with large pulse durations is expedient to define the pulse interval as the duration of the pause between two pulses, i.e. the time interval between the falling gradient of a heating laser pulse and the rising gradient of the next heating laser pulse. Preferably the temporal pulse interval between the first and the at least second heating laser pulse should be predetermined as greater than the thermal relaxation time of the tissue.

Previous knowledge about the thermal relaxation time exists in the literature, e.g. Brinkman and Birngruber, "Selective Retina Therapy" in Z. Med. Phys. 17 (2007), pp. 6-22. There it is stated that the thermal relaxation time depends on the size and structure of the object heated with laser light and for an assumed homogenous RPE absorber layer of 4 μm in thickness is around 64 μs. The authors also conclude: "If the aim is to heat all the RPE cells evenly, without significantly heating the surroundings, pulse durations of approximately 5-30 μs are suitable. If, on the other hand, it is intended to produced pronounced peak temperatures on the melanosomes, pulse durations of <5 μs should be chosen. At pulse durations of >50 μs the cellularly limited temperature increase is lost". This also indicates the aforementioned, preferred interval for the pulse durations.

Particularly preferably, the temporal pulse interval is selected to be such that the temperature increase in the tissue achieved with the first heating laser pulse is largely eliminated before triggering the second pulse, i.e. the tissue has returned to the basic temperature of the tissue before the start of the irradiation, typically 37° C.

Whereas the first heating laser pulse serves to obtain information about the tissue in the selected laser spot, according to the invention, the second heating laser pulse brings about heating just there to a target temperature for a therapeutic effect. The second heating laser pulse is typically richer in energy than the first heating laser pulse i.e. the product of laser power and pulse duration is typically greater for the second heating laser pulse than for the first heating laser pulse.

It is considered as advantageous if the first and the second heating laser pulse have the same pulse duration and the laser power is only regulated for the second heating laser pulse. In the high-performance laser diodes developed to date this can easily be achieved through regulating the direct power supply. Through this, expensive optical components for electronically-controlled shielding or diverting the laser light, such as, for example, an acusto-optical modulator are unnecessary. Nevertheless, the use of light modulators or varying the applied power are also covered by the framework of the present invention.

Subject to the condition that the emission power of the laser light source on switching a heating laser pulse on and off shows a sufficiently steep rising and falling gradient, and in between them a smooth, constant plateau course, only two significant volume change signals are in fact generated, if the energy irradiated during the gradient duration, at, corresponds with the typical pulse energies of sample pulses of the detection to date. For photoacoustic detection, sample pulses of energy 5 μJ are known to be sufficient. With a laser power of $P_{max}$=10 W, this corresponds with a gradient duration of at δt=1 μs, in which the applied laser power linearly increases from zero to the maximum value in the first approximation and then decreases again.

Seen as a very particular advantage of the invention is that the evaluation of the volume change as a result of the first heating laser pulse for determining an estimated value for the temperature increase can also be easily used on the at least second heating laser pulse, so that after the end of processing a laser spot, an estimated value for the actual therapeutically active target temperature brought about by the laser is produced. This estimated value can be shown to the treating doctor in real time and also documented, i.e. electronically saved, and can be compared with a target temperature wanted by the doctor. The user thus has effect monitoring available, and on request a stored therapy protocol, that he/she could also use as electronic proof of treatment or to document a therapy history.

If heating laser pulses are applied in the μs time range with laser powers in the W range onto absorbent tissue, during the power changes dp1 and dP2 of the laser—on the rising (dp1) and falling (dp2) laser pulse gradient—well detectable, rapid volume changes occur through expansion dV1 and contraction dV2 of the tissue, if the power changes occur rapidly enough within short gradient durations dt1 and dt2 respectively. The heating laser pulse gradients thus determine the measuring signals to be recorded, namely as the tissue responses directly to switching the laser on and off. In the case of pulses with a constant plateau course, taking into account the rises in the laser power on the pulse gradients is sufficient for signal evaluation.

The speeds of the expansion dV1/dt1 and contraction dV2/dt2 can be directly measured opto-interferometrically in that position displacements of tissue layers, for example the tissue surface, are followed. During the gradients of the heating laser pulse, these speeds are at their greatest and allow estimation of the thermal expansion coefficient of the tissue, which in turn can be derived from preliminary work as a temperature-dependent material parameter over a broad temperature range.

At the same time, the rapid volume changes trigger pressure waves in irradiated areas which propagate through the tissue and can be recorded by an ultrasonic receiver as a time-dependent pressure signal (pressure transient). In this case too, the previously known temperature-dependency of the Grüneisen coefficient is used to directly extrapolate the temperature from the pressure transients. Considered as concrete measured values dD1 and dD2 can, for example, be the maximum amplitude of the pressure transients or the integral or the pressure transients over a period of increased amplitude or also the frequencies of the pressure transients.

Experimentally, with acoustic detection it was found that the ratio of the pressure measurement signals from the end of the laser pulse to the start of the laser pulse can be used as a measure for heating of the tissue during the heating laser pulse if the power changes and gradient durations at both pulse ends are the same. However, as a rule this is not the case, but the laser pulse gradients can either be measured during every pulse or—with sufficient stability of the laser from pulse to pulse—from previously tabulated data that the manufacturer of the laser light source may be able to supply.

In the case of different gradient courses at the start and end of the heating laser pulse, the ratio of the pressure measurement signal can be standardised to the gradient rises, for example in accordance with $$\alpha = \frac{\frac{dD2}{\Delta P2}}{\frac{dD1}{\Delta P1}}$$

The value $\Delta P$ can here be introduced as the maximum rise of the laser gradients $$\Delta P = \frac{dP}{dt}(t = t_{max})$$

or alternatively as the mean rise $$\Delta P = \frac{1}{\delta t}\int_0^{\delta t}\frac{dP}{dt}(t')$$

averaged over the gradient duration $\delta t$. Other standardisations in this sense are also possible.

The steeper the power changes of the laser light, the faster the volume change of the tissue takes place. This then brings about higher expansion and contraction speeds and higher pressure amplitudes.

With regard to acoustic detection, the value $\alpha$ is determinable, which, expressed in other words, shows the ratio of the energies of the triggered pressure wave to the irradiated laser energy in each case for the pulse end gradient and pulse start gradient in relationship to each other. From the ratio $\alpha$ and the known temperature dependency of the Grüneisen coefficient of the tissue, the produced temperature increase of the tissue up to the end of the pulse can be derived.

Particularly with pulse durations that are smaller than the thermal relaxation time of the tissue, a temperature gradient is produced in radiation propagation direction z in accordance with the absorption and diffusion $\mu a(z)$ and $\mu s(z)$ of the radiation. The value $\alpha$ therefore only leads to a mean weighted temperature value, which depends on all irradiation and tissue parameters.

In order to approximately extrapolate the temperature increase, the temperature-dependent course of the Grüneisen coefficient as well as the starting temperature before irradiation (body temperature, room temperature) must be known. The temperature dependency of the Grüneisen coefficient be approximated, for example with a quadratic equation in the form $$\Gamma(T) = C * \left[(T^2 - T_0^2) - 2T_m(T - T_0)\right]$$

for tissue in the temperature range from $0 = 100°$ C. For the case of retinal tissue from pigs in a cuvette, the maximum of the parabola $T_m = 105.4°$ C. and the zero crossing $T_0 = -21°$ C. was approximated (from: Kandula et al., Journal of Biomedical Optics 11(4) 2006), where C is a proportionality constant.

One possibility of calculating the mean temperature increase in the tissue $\overline{T_{Heiz}}$ is to calculate this directly via a fit function. From the aforementioned parabolic approximation, the mean temperature increase is $$\overline{T_{Heiz}} = T_m \pm \sqrt{\alpha B + (T_m - T_0)^2}$$

with $$B = T_B^2 - T_0^2 - 2T_m \cdot (T_B - T_0)$$

$T_B$ is the basis temperature (e.g. room temperature or body temperature). In order, from the mean temperature increase $\overline{T_{Heiz}}$ to be able to extrapolate the often more interesting maximum temperature increase $T_{max}$ at the place of the higher temperature, a constant f can be determined.

$$T_{max} = (\overline{T_{Heiz}} - T_B) \cdot f + T_B$$

In general, the constant f depends on the irradiation geometry and irradiation duration as well as the thermal tissue parameters. In the case of a stretched homogeneous absorber without diffusion, on irradiation with pulse durations below the thermal relaxation time this results in f=2. Generally speaking, f can be determined for special sample type or in this case tissue classes via theoretical model or also experimentally (e.g. by way of thermal sensors, temperature-dependent fluorescing nanoparticles etc.).

To control the irradiation process at a defined target temperature $T_{Ziel}$ at least two heating laser pulse are applied, wherein the first heating laser pulse has an energy $E_1$ which does not yet let the target temperature be reached and preferably also causes no thermal damage to the tissue. From the temperature $\overline{T_{Heiz}}$ measured after the first pulse, the energy $E_2$ of the second hearing laser pulse can be adjusted by way of setting the power and/or pulse duration so that the target temperature is reached after the end of the second pulse, for example through $$T_{Ziel} = (\overline{T_{Heiz}} - T_B) * \frac{E_2}{E_1} + T_B$$

Several pulse can also be applied to approach the target temperature in stages.

As long as the heat energy deposited in the tissue through laser absorption cannot leave the irradiated volume via thermal transport mechanisms (thermal inclusion), it does not in principle matter whether the increased energy $E_2$ is achieved through increasing the power or the pulse duration of the at least one second heating laser pulse. Initially only the products of power and pulse duration are relevant. However, it is seen as advantageous not to increase the second pulse duration, but to set it equal to the first duration and only increase the power. Thermal transport is time-dependent and the transport processes during the second heating laser pulse are naturally most similar to those of the first heating laser pulse. In addition, it is seen that during power regulation of the laser light source, switching on and off procedures can lead to different laser power courses at different pulse durations. By dispensing with a light modulator to control the emission of the continuously activated laser, and operating the laser with power pulses instead, with different pulse durations it cannot necessarily be assumed that the pulse form is maintained. This can complicate the evaluation of the measuring values and is easily avoidable if all pulse durations are selected to be the same.

It is advantageous to select the pulse sequence so be such that between the individual pulses as complete as possible cooling of the tissue to the basis temperature takes place. Alternatively, the remaining residual heat can be included in the calculation.

As has already been mentioned, it is an important advantage of the invention that the actually attained target temperature in the tissue can be measured, in that the detection device records the volume changes respectively caused by the increasing and decreasing slope of the second heating laser pulse and supplies the measuring results to the arithmetical unit which determines and displays and/or logs an estimated value for the temperature increase during the second heating laser pulse. Such a numerical, objective effect assessment for the laser treatment is seen as important progress compared to therapy lasers used to date.

Moreover, with power lasers of the order of 5 W to 100 W, access is opened to thermos-mechanical therapy approaches which centre on cell disruption through evaporation. Here too, treatment and even a certain effect monitoring with the same laser device according to the invention is possible if only the software of the arithmetical unit is expanded.

Preferably, in this case, i.e. intended thermomechanical tissue damage with target temperature of, for example, more than 140° C., as of the start of the second heading laser pulse, the arithmetic unit is configured to determine and log the difference between the time of onset of a volume change on the rising gradient of the heating laser pulse and the next time of onset of a volume change. If this measured difference is smaller than the second pulse duration, the measuring signal showing the volume change arrives early and cannot therefore originate from the falling laser gradient. Rather, volume changes are recorded that are due to the formation of micro-bubbles in the tissue. Bubble formation is usually associated with pressure amplitudes that are up to two orders of magnitude greater than purely thermally triggered pressure amplitudes when the gradients of the heating laser pulses are not to steep. They can therefore practically not be overseen and the time of their onset marks the start of bubble formation. In turn, the time difference between the start of bubble formation and the end of the heating laser pulse is measurable and can be used as a measure for the thermo-mechanical treatment dose. With known pulse duration, this measure can be directly seen from the time difference determined in the arithmetic unit between the start of the laser pulse and the start of bubble formation.

The invention will be described in more detail below by way of the figures. In these:

Figure 1:
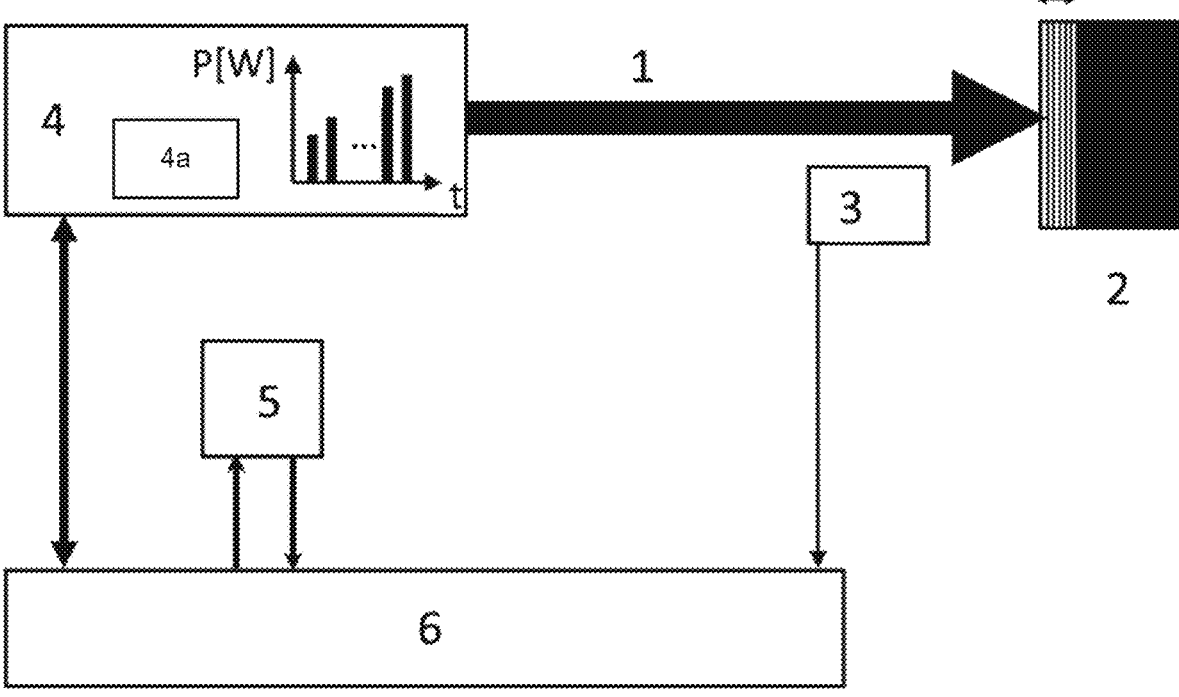
FIG. 1 shows a sketch of the laser system with ab arithmetic unit and detector for volume change signals.

Seen in FIG. 1 is a sketch of the laser device according to the invention in an embodiment for the therapy of the retina. In the sketch, the light guide means, the applicator as well as the trigger for the applicator are not shown.

A laser source (4) emits heating laser pulses (1) onto tissue (2). A detection device records the change in volume of the tissue and generates electrical signals which are supplied to an arithmetic unit (6). The arithmetic unit (6) can be a programmable microprocessor or personal computer. It processes the raw data arriving from the detection device (3)—and, if required, stores these in a non-volatile manner—and on the basis of the processing results determines control commands to the laser (4). A control device for the laser (4) is not shown separately, but instead, is usually integrated into the laser (4) in a structural unit. If, as preferably assumed here, the operating current strength of the laser (4) is varied to control the laser power, the control device can be designed as a simple analogue circuit(4a) which directly transfers voltage values originating from the arithmetical unit (6) in currents. Alternatively, the control device can also be integrated into the arithmetic unit (6). The control device can also be designed to digitally receive metacommands of the arithmetic unit (6) such as, for example, values for pulse duration and pulse power and to convert these into analogue signals for controlling the laser (4).

According to the invention the laser (4) has an emission power of the order of 5 W to 100 W. Here, as an example, integrated into the laser (4) and not shown separately are preferably means for the time recording of the emitted laser power of at least one portion of the laser light (1). The detected measured values of the laser power are supplied to the arithmetic unit (6), wherein the arithmetic unit (6) determines the rises of the power gradients for the laser pulses. Such irradiation monitoring is current state of the art. In the case of very stable laser light sources, the compilation of a table with gradients for laser pulses of different pulse durations and power can be considered instead of constantly repeated measurements.

An operating device (5) intended for the user input of irradiation parameters into the arithmetic unit (6) is preferably configured to show the user selectable intervals for irradiation parameters, wherein the interval limits depend hierarchically on user inputs. This means that the operating device (5) can be in a position to adhere to certain safety rules and to decline entries that contradict these rules. When using a power laser with a high potential for causing damage, particularly in retinal therapy, incorrect parameter settings by the user can therefore be averted at an early stage. As an example, and preferably, the operating device (5) can be designed to select the power of the first heating laser pulse based on the user's input of the pulse duration in such a way that the first heating laser pulse does not cause any lasting tissue damage. It is also advantageous if the operating device (5) is designed only to allow, as user inputs for the temporal pulse interval between the first and the at least second heating laser pulse, values that are greater than at least one thermal relaxation time of the tissue predetermined from the user input for the first pulse duration. Here, hierarchical dependency means that some of the user's selection options are given priory in implementation while other selection options are considered as subordinate and, subject to predetermined, for example, programmed, safety rules are appropriately restricted depending on the higher-priority user inputs.

In this respect, the operating element (5) can comprise its own processor for data processing and a data memory for non-volatile data storage.

The operating element (5) can be designed in such a way that envisaged as user inputs are at least the target temperature and laser pulse duration—as priority for example—as well as optionally and subordinately the temporal laser pulse interval and the first power of the first heating laser pulse. In addition, the processor of the operating element (5) can perform an encryption algorithm in order to encrypt data transmitted by the arithmetic unit (6) together with the user inputs and thereby save them in an inseparable and unmodifiable manner. Such secured data are subsequently only readable together and can be used as an authenticable treatment protocol (also with a time stamp).

Figure 2:
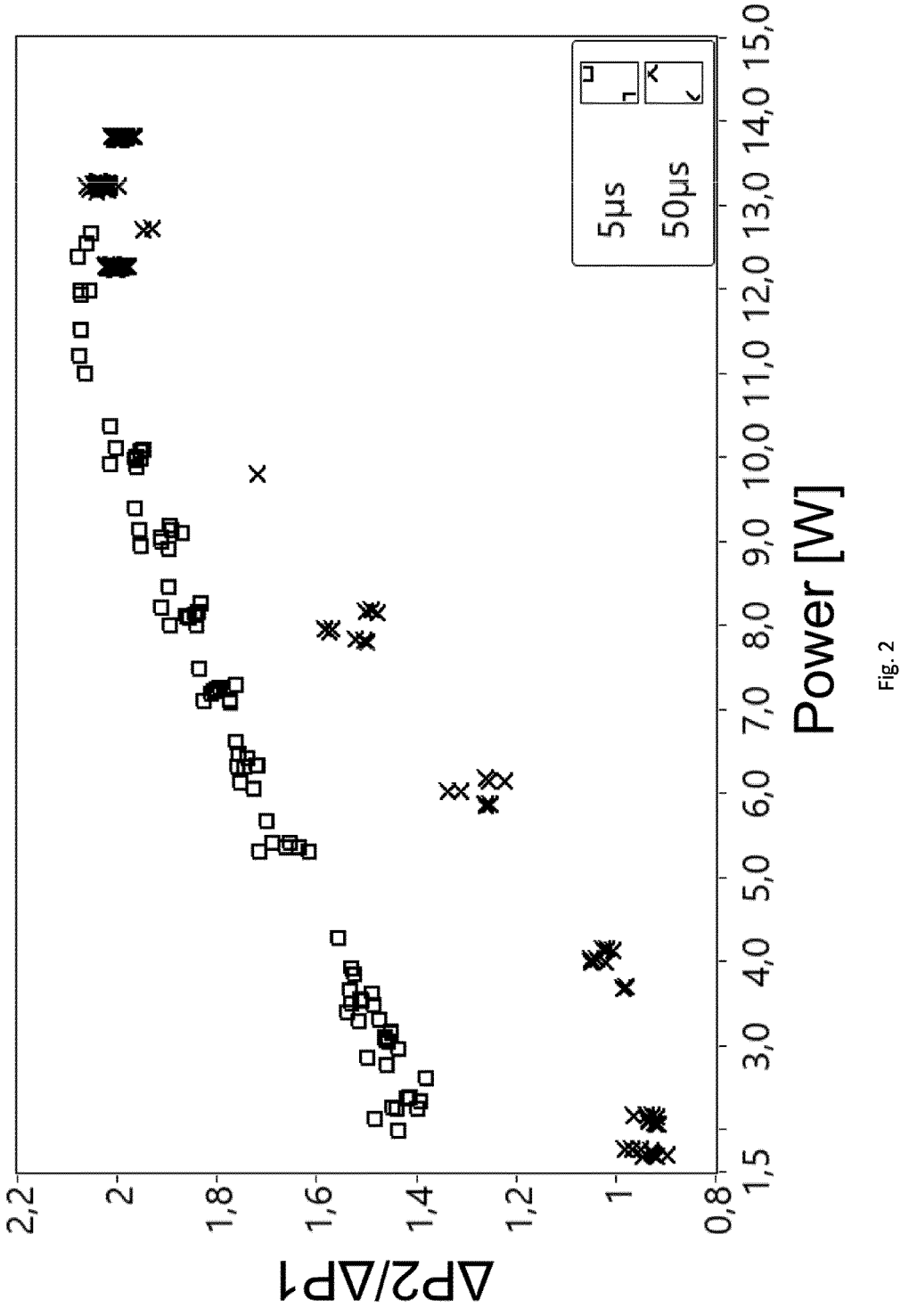
FIG. 2 shows experimental data on the gradients rises of the laser light at various pulse durations and power using the example of a diode laser.

The variation of the ratio of the gradients rise $\Delta P_2/\Delta P_1$ of the heating laser pulse has been experimentally investigated with variation in the pulse duration and laser power. FIG. 2 shows measuring values for pulse durations of 5 μs and 50 μs at powers up to 14 W solely as an example illustration. It is shown the ratios of the gradients rise of the pulse—as well as the gradients rise themselves—change with the applied power through changed stimulation conditions (incl. pump flow) of the laser. It is clear that the pulse-wise measurement of the gradient rises is expedient for the evaluation described here, if one does not want to carry out laborious calibration of the laser light source. Furthermore, ageing effects of the laser are possible so that one-off ex-works calibration is not necessary always sufficient.

Figure 3A:
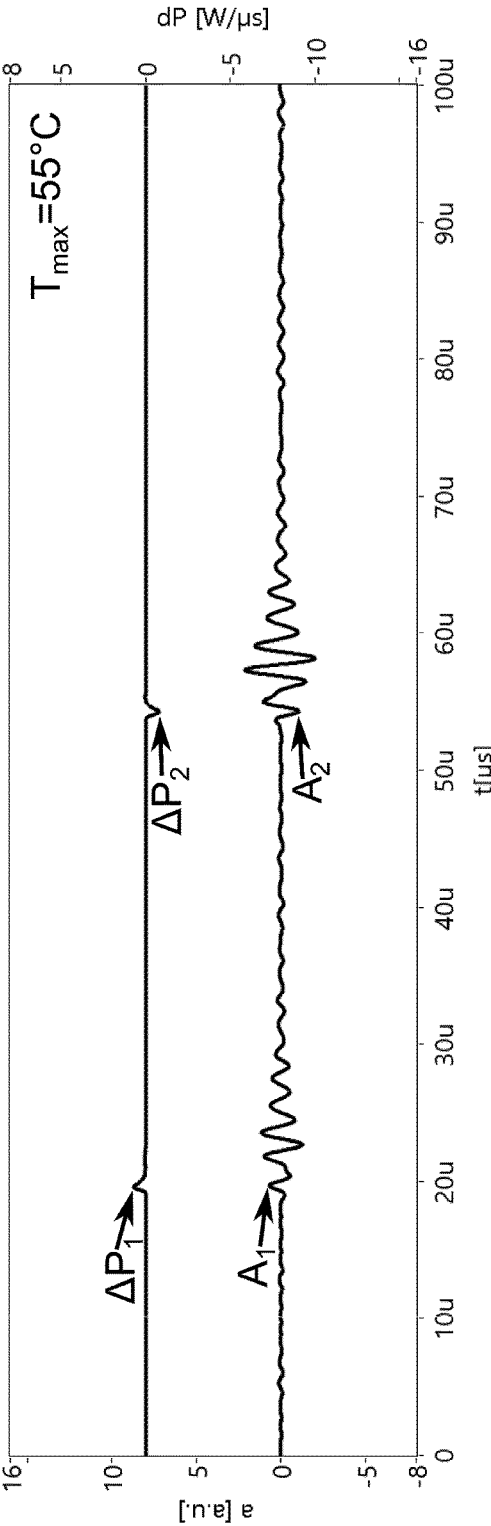
FIGS. 3a-3c show experimentally measured (time-shifted) pressure transients for heating laser pulses of comparable pulse durations with different powers.
Figure 3B:
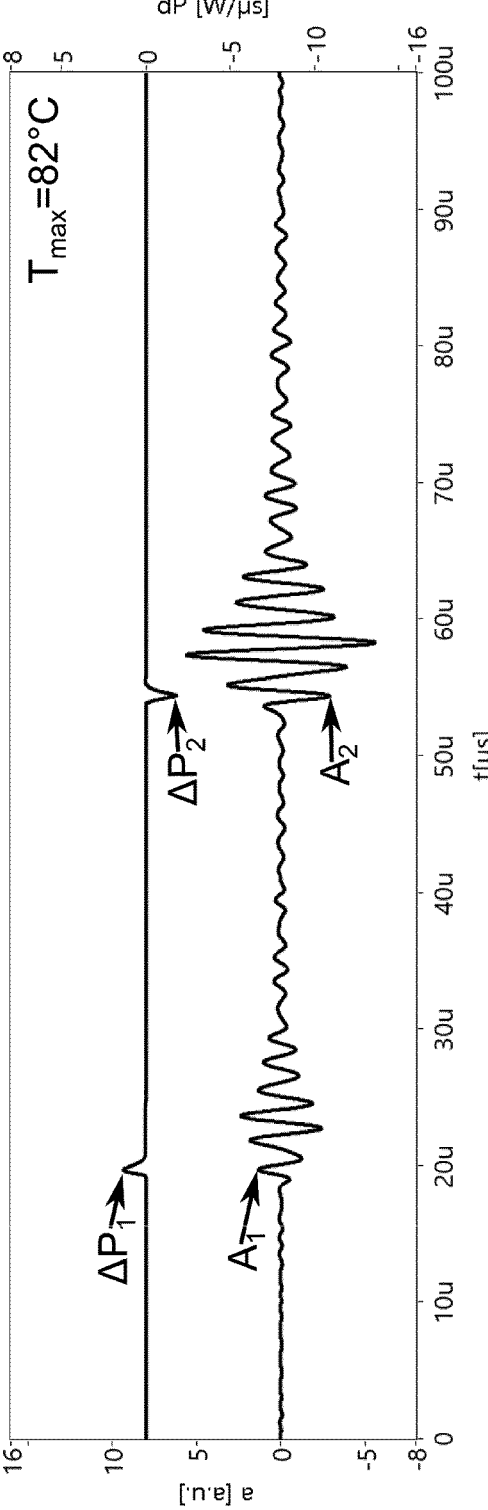
Figure 3C:
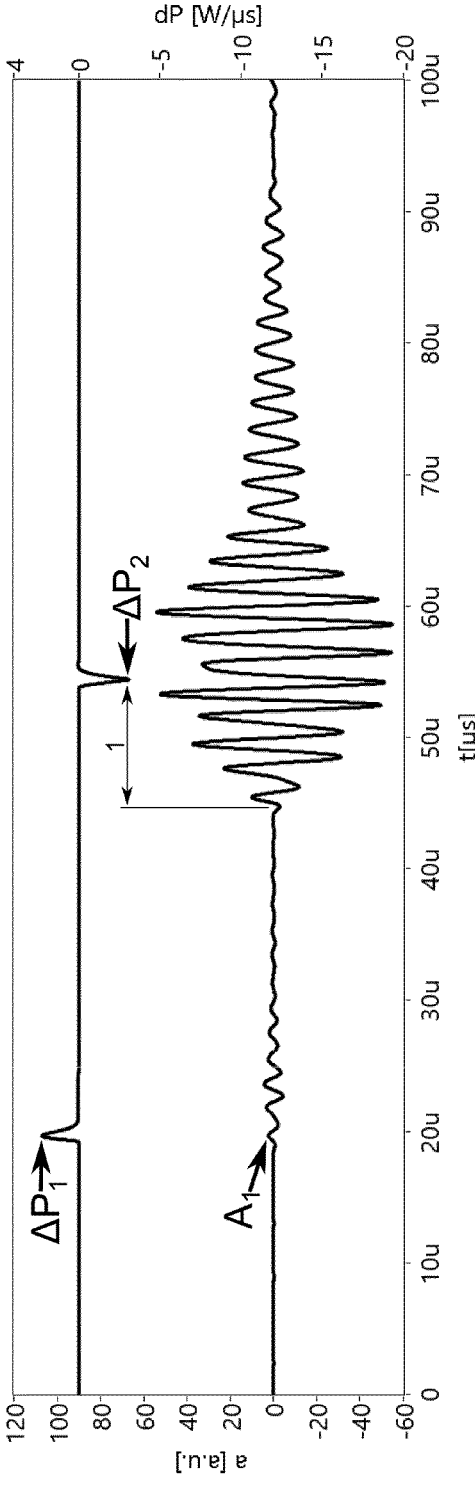

FIGS. 3a-3c show three examples of measured pressure transients at different laser powers. The pressure transients are in each case the lower curves, the derivations of the heating laser pulses the top curves. For the sake of presentability of the comparison in all plots they are standardised in such a way that the first maximum of the first pressure transient in terms of the numerical value corresponds to the maximum gradient ΔP1 of the rising gradient of the first heating laser pulse. It can easily be seen how high the contribution of a temperature increase is to a pressure transient at the end of the heating laser pulse. The acoustic duration from the sample to the sensor was removed for better presentation, i.e. the pressure transients were displaced by the duration.

FIG. 3a show pressure transients in the case of irradiation with 614 mJ/cm²: the irradiated pulse of 35 μs pulse duration has two gradient rises ΔP1 and ΔP2 which each trigger a pressure transient A1 and A2. Here, the pressure transients are shown on the same time axis as the heating laser pulses, i.e. displaced by the constant signal duration from the retina to the ultrasonic transducer for better assignment. Energy measure figures dD1 and dD2 are assigned to the pressure transients, which here, for example, at determined from the maximum amplitudes of the signals A1 and A2. From this the ratio α is calculated and $T_{Heiz}$ as the temperature at the end of pulse is 55° C. Such a temperature increase for a short time does not generally damages living retinal tissue. The shown curves represent an example of the first heating laser pulse of the method according to the invention.

FIG. 3b shows pressure transients in the case of irradiation with 1245 mJ/cm²: when applying a pulse with double the power compared to FIG. 3a, the same signals are seen with now increased values. The laser pulse gradients rise more quickly and the amplitudes of the pressure transients are clearly increased. With the same calculations as for FIG. 3a, this results in a temperature of 82° C. at the end of the pulse which is already in the usual range for the target temperature of photocoagulation. FIG. 3b thus represents a possible second heating laser pulse according to the invention which directly results in a therapeutic effect.

FIG. 3c show pressure transients in the case of irradiation with 1488 mJ/cm²: this irradiation leads to bubble formation in the tissue. The second pressure transient already occurs before the laser power decrease. It is thus not based on thermoelastic relaxation on cooling of the tissue, but on material evaporation. The double arrow 1 shows the time difference of onset of the acoustic signal and the end of irradiation. The modified scales are compared with FIGS. 3a and 3b. The amplitude, increased by a factor of 10, is also an indicator of microbubble formation and confirms the assumption. As the power of the irradiation as well as the time to microbubble formation are known, it can be determined with which irradiation strength the microbubble formation temperature over approximately 140° C. can be achieved. The duration of thermo-mechanical disruption up to the end of the heating laser pulse can also be used as a dose measure and, possibly, though adjusting the laser, be adapted and optimised for further laser pulses.

It should also be noted here, that the curves of FIGS. 3a-3c were not recorded at the same laser spot. Therefore the absorption coefficients of the tissue differ between the experiments.

What is claimed is:

1. A laser therapy device for therapy of a living tissue, comprising:
a pulsed laser light source which emits laser light with an emission power in the range of 5 W to 100 W for irradiation of the tissue, a detection device for detecting time-dependent changes in volume resulting from laser absorption in the tissue, a processor for evaluating the detected volume changes and outputting control commands to a control circuit for controlling the power of the laser light irradiated into the tissue, wherein:
each triggering of tissue irradiation causes a first heating laser pulse with a first power and a first pulse duration and at least a second heating laser pulse with a second power and a second pulse duration to be applied to the tissue at a predetermined temporal pulse interval;
the detection device optically or acoustically records the detected volume changes resulting from a rising power gradient of the first heating laser pulse and supplies corresponding measured values to the processor;
the processor, based on the measured values and taking into account at least the rising power gradient of the first heating laser pulse, determines an estimated value for a temperature increase in the tissue during irradiation of the first heating laser pulse; and
from the estimated value, the processor generates a command for the control circuit, which causes the control circuit to adjust the second power and/or the second pulse duration of the second heating laser pulse so that the irradiation of the second heating laser pulse heats the tissue to a predetermined target temperature.

2. The laser therapy device according to claim 1, wherein the control circuit is set up so that pulse durations of all heating laser pulses are the same.

3. The laser therapy device according to claim 1, wherein the detection device records the detected changes in volume caused by the rising and falling power gradient of the second heating laser pulse and supplies a corresponding measured value to the processor, wherein the processor determines and displays and logs an estimated value for a temperature increase during the irradiation of the second heating laser pulse.

4. The laser therapy device according to claim 1, wherein the emitted laser power is detected and measured values of the emitted laser power are provided to the processor to determine the rises in the power gradients.

5. The laser therapy device according to claim 1, wherein the detection device is designed for recording thermally triggered pressure waves in the irradiated tissue, and comprises at least one ultrasonic transducer that records a pressure transient and outputs the recorded pressure transient as measured values.

6. The laser therapy device according to claim 1, wherein the detection device is designed for the optical recording of thermally triggered movements of light-diffusing or reflecting tissue layers in the irradiated tissue, and comprises an interferometer and at least one photodetector, which records time-variable light intensity and outputs the time-variable light intensity as measured values.

7. The laser therapy device according to claim 1, wherein the processor is to determine and log, as of the start of the second heating laser pulse, a difference between a time of onset of a volume change on the rising gradient of the second heating laser pulse and a next time of onset of a volume change.

8. The laser therapy device according to claim 1, wherein irradiation parameters are user-selectable in intervals and input into the processor.

9. The laser therapy device according to claim 8, wherein the first power of the first heating laser pulse is based on user input for the first pulse duration in such a way that the first heating laser pulse does not cause any lasting tissue damage.

10. The laser therapy device according to claim 8, wherein the user is enabled to input only values for the temporal pulse interval between the first heating laser pulse and the second heating laser pulse that are greater than a thermal relaxation time of the tissue predetermined from at least the user input for the first pulse duration.

\* \* \* \* \*